United States Patent [19]

Hartwell et al.

[11] Patent Number: 4,983,735

[45] Date of Patent: Jan. 8, 1991

[54] PREPARATION OF ALCOHOL-EXTENDED AND AMINE-EXTENDED PIPERAZINES

[75] Inventors: George E. Hartwell; Robert G. Bowman; David C. Molzahn, all of Midland, Mich.

[73] Assignee: The Dow Chemical Company, Midland, Mich.

[21] Appl. No.: 221,710

[22] Filed: Jul. 20, 1988

[51] Int. Cl.$^5$ .................. C07D 295/08; C07D 295/12
[52] U.S. Cl. ...................................... 544/402; 544/401
[58] Field of Search ................................ 544/401, 402

[56] References Cited

U.S. PATENT DOCUMENTS 4,927,931  5/1990  Molzahn et al. .................... 544/357

*Primary Examiner*—Cecilia Shen

[57] ABSTRACT

A process for preparing alcohol-extended and amine-extended piperazines comprising contacting a difunctional aliphatic alcohol with a reactant amine, wherein at least one of the aliphatic alcohol or the reactant amine contains a piperazine moiety, in the presence of a catalyst containing a tungsten heteropoly acid. For example, monoethanolamine reacts with piperazine in the presence of a 12-tungstophosphoric acid catalyst to yield predominantly N-(2-aminoethyl)piperazine, which is an amine-extended piperazine.

26 Claims, No Drawings

PREPARATION OF ALCOHOL-EXTENDED AND AMINE-EXTENDED PIPERAZINES

BACKGROUND OF THE INVENTION

This invention relates to a process for preparing alcohol-extended piperazines, such as N-(2-hydroxyethyl)piperazine, and amine-extended piperazines, such as N-(2-aminoethyl)piperazine, bis(piperazinylalkanes), and oligo(piperazinylalkanes). Hereinafter, bis(piperazinylalkanes) will be referred to as bispiperazines.

Alcohol-extended and amine-extended piperazines are useful intermediates in the preparation of melt adhesive polymers and fine industrial chemicals, including veterinary antihelmintic pharmaceuticals, insecticides, and high temperature lubricating oils.

U.S. Pat. No. 3,364,218 teaches the self-condensation of N-(2-hydroxyethyl)piperazine to poly-1,4-ethylenepiperazine in the presence of hydrogen and a solid acid catalyst, such as silica-alumina, alumina, tungsten oxide, aluminum phosphate, and acid clays. It is difficult to control the degree of polymerization in this process. Accordingly, it is difficult to obtain high yields of N-(2-aminoethyl)piperazine, bis(piperazinylethanes), tris(piperazinylethanes), or other specific oligo(piperazinylethanes). Moreover, cyclic compounds, such as 1,4-diaza-[2.2.2]-bicyclooctane, are produced as undesirable by-products. In addition, the catalysts employed in this process lose their physical integrity in the presence of amines and water: therefore, the process is hampered by catalyst losses and separation problems.

U.S. Pat. No. 4,552,961 discloses a process for the preparation of polyalkylene polypiperazines comprising reacting piperazine with alkylene glycols or alkanolamines in the presence of a catalyst of phosphorus amide. Disadvantageously, this catalyst is homo and must be separated from the product stream.

It would be advantageous to have a catalytic process for preparing alcohol-extended and amine-extended piperazines. It would be more advantageous if the degree of polymerization of such a process could be controlled, and selective alcohol-extended and amine-extended piperazines could be prepared in high yields. It would be even more advantageous, if the catalyst for such a process was insoluble in the reaction mixture. With an insoluble catalyst the problems of leaching, plugging, and catalyst separation would be avoided, and the amination process would be more suitable for industrial adaptation.

SUMMARY OF THE INVENTION

This invention is a process for preparing alcohol-extended and amine-extended piperazines comprising contacting in the presence of a catalyst a difunctional aliphatic alcohol with a reactant amine, wherein at least one of the aliphatic alcohol or reactant amine contains a piperazine moiety. The catalyst is a composition containing a tungsten heteropoly acid. The contacting is conducted under reaction conditions such that a mixture of alcohol-extended and/or amine-extended piperazines is produced.

Advantageously, the process of this invention is capable of producing a wide range of alcohol-extended and amine-extended piperazines in high selectivity. Moreover, the process of this invention does not produce significant amounts of undesirable cyclic by-products. More advantageously, the catalyst of this invention is insoluble in the reaction mixture; therefore, catalyst losses are minimized and separation of the product stream from the catalyst is relatively easy. These combined advantages render the process of this invention suitable for industrial use.

Alcohol-extended piperazines and amine-extended piperazines are useful intermediates in the preparation of melt adhesive polymers and fine industrial chemicals, including veterinary antihelmintic pharmaceuticals, insecticides, and high temperature lubricating oils.

DETAILED DESCRIPTION OF THE INVENTION

The products of the process of this invention are alcohol-extended and amine-extended piperazines. These products are described in detail hereinafter; but, are easily illustrated by the following three examples, The first comprises N-(2-hydroxyethyl)-piperazine, which is an alcohol-extended piperazine and which is prepared by reacting ethylene glycol with piperazine. The second comprises N-(2-aminoethyl)-piperazine, which is an amine-extended piperazine and which is prepared by reacting monoethanolamine with piperazine. The third comprises bis(piperazinyl)ethane, which is also an amine-extended piperazine and which is prepared by reacting N-(2-hydroxyethyl)-piperazine with piperazine. It is observed that in each example the products are linearly-extended materials obtained by the condensation of a difunctional alcohol with a reactant amine.

At least one of the reactants must contain a piperazine moiety in order for the process to yield an alcohol-extended or amine-extended piperazine product. Accordingly, it is within the scope of this invention for the difunctional alcohol to contain the piperazine moiety, as in the amination of N-(2-hydroxyethyl)-piperazine by ammonia or a primary aliphatic amine. Likewise, it is within the scope of this invention for the reactant amine to contain the piperazine moiety, as in the amination of ethylene glycol by piperazine or N-(2-aminoethyl)piperazine. It is also within the scope of the invention for both the difunctional alcohol and the reactant amine to contain a piperazine moiety, as in the amination of N-(2-hydroxyethyl)-piperazine by piperazine to yield bis(piperazinyl)-ethane. It is to be understood, therefore, that at least one of the difunctional alcohol or the reactant amine must contain a piperazine group.

The difunctional aliphatic alcohols which are employed in the process of this invention include any aliphatic alcohol containing (a) at least one hydroxyl moiety bound to a primary carbon atom, and (b) at least one additional moiety selected from the group consisting of hydroxyl, primary amine or secondary amine functionalities. Examples of suitable difunctional alcohols include diols such as ethylene glycol and propylene glycol, triols such as glycerol, and higher polyols; polyether polyols such as diethylene glycol, polypropylene glycols, and higher homologues: alkanolamines such as monoethanolamine and N-(2-aminoethyl)ethanolamine; polyether amino alcohols such as 2-($\beta$-aminoethoxy)ethanol; and hydroxyalkyl-substituted piperazines, such as N-(2-hydroxyethyl)piperazine, N,N'-bis(2-hydroxyethyl)piperazine, and N-(2-hydroxyethyl)bispiperazines. The difunctional alcohols are not limited to the aforementioned examples, and other equally suitable difunctional alcohols can be employed in the practice of this invention.

In those reactions wherein the difunctional alcohol does not contain a piperazine moiety, the preferred difunctional alcohols are represented by the general formula:

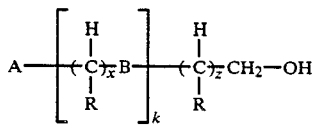

wherein A is OH or NHR: each B is independently NR or O; each R is independently hydrogen, hydroxy, amino (NH$_2$), a lower alkyl moiety of C$_1$-C$_{12}$ carbon atoms such as methyl, ethyl or propyl, a hydroxyalkyl or aminoalkyl moiety of C$_1$-C$_{12}$ carbon atoms, or a monocyclic aromatic moiety, such as phenyl, or tolyl: x is an integer from 2 to about 12: k is an integer from 0 to about 150; and z is an integer from 1 to about 12. Some examples of difunctional alcohols which satisfy this formula include monoethanolamine, ethylene glycol, propylene glycol, and N-(2-aminoethyl)ethanolamine. Preferably, R is hydrogen. More preferably, R is hydrogen, x is 2, and z is 1. Most preferably, R is hydrogen, A is NH$_2$, k is 0, z is 1, and the difunctional alcohol is monoethanolamine.

In those reactions wherein the difunctional alcohol contains a piperazine moiety, the preferred difunctional alcohols are represented by the general formula:

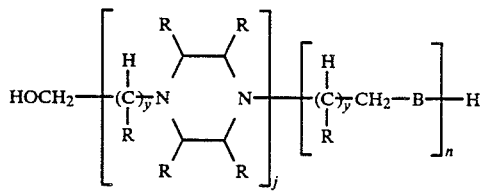

wherein each B is independently NR or O; each R is independently hydrogen, hydroxy, amino (NH$_2$), a lower alkyl moiety of C$_1$-C$_{12}$ carbon atoms such as methyl, ethyl or propyl, a hydroxyalkyl or aminoalkyl moiety of C$_1$-C$_{12}$ carbon atoms, or a monocyclic aromatic moiety, such as phenyl, or tolyl; each y is independently an integer from 0 to about 12; j is an integer from 1 to about 6: and n is an integer from 0 to about 6. Some examples of difunctional alcohols which satisfy this formula are N-(2-hydroxyethyl)piperazine, N-(2-hydroxyethyl)bispiperazine, N,N'-di(2-hydroxyethyl)piperazine, and N,N'-di(2-hydroxyethyl)bispiperazine. Preferably, R is hydrogen. More preferably, R is hydrogen, each y is independently 1 or 2, j is 1 or 2, n is 0-2, and B is NR. Most preferably, R is hydrogen, y is 1, j is 1, n is 0, and the compound is N-(2-hydroxyethyl)piperazine.

The reactant amines which are employed in the process of this invention include ammonia and any primary or secondary aliphatic amine which is capable of aminating the difunctional alcohol. Examples of suitable reactant amines include primary and secondary monoamines such as ethylamine, propylamine, n-butylamine, hexylamine, octylamine, diethylamine, dipropylamine, dibutylamine, dihexylamine, dicyclohexylamine, and dioctylamine; linear and branched alkylene diamines or polyamines such as ethylenediamine, propylenediamine, diethylenetriamine, triethylenetetramines, and tetraethylenepentamines: alkylene ether polyamines such as 2-(β-aminoethoxy)ethylamine; piperazine and oligo(piperazinyl alkanes) such as bispiperazines and trispiperazines; aminoalkyl-substituted piperazines such as N-(2-aminoethyl)piperazine and N,N'-bis(2-aminoethyl)-piperazine; and mixtures of the above-identified amines. While the aforementioned reactant amines are representative of those which are suitable in the process of this invention, other reactant amines not recited herein may be equivalent and equally suitable.

In those reactions wherein the reactant amine does not contain a piperazine moiety and is an alkylenepolyamine or alkylene ether polyamine, the preferred species are represented by the general formula:

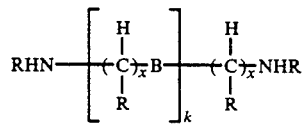

wherein each B is independently NR or O; each R is independently hydrogen, hydroxy, amino, a lower alkyl moiety of C$_1$-C$_{12}$ carbon atoms such as methyl, ethyl or propyl, a hydroxyalkyl or aminoalkyl moiety of C$_1$-C$_{12}$ carbon atoms, or a monocyclic aromatic moiety, such as phenyl, or tolyl; each x is independently an integer from 2 to about 12, and k is an integer from 0 to about 150. Some examples of reactant amines which satisfy this formula include ethylenediamine, diethylenetriamine, 2,2'-di(aminoethyl)ether, and triethylenetetramine. Preferably, B is NR and the amine is an alkylenepolyamine. More preferably, B is NR and R is hydrogen. Most preferably, B is NR, R is hydrogen, each x is 2, and the amine is an ethylenepolyamine.

In those reactions wherein the reactant amine contains a piperazine moiety, preferred piperazines or aminoalkyl-substituted piperazines are represented by the general formula:

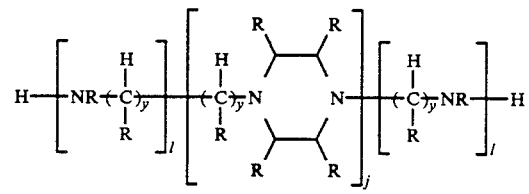

wherein each R is independently hydrogen, hydroxy, amino, a lower alkyl moiety of C$_1$-C$_{12}$ carbon atoms such as methyl, ethyl or propyl, a hydroxyalkyl or aminoalkyl moiety of C$_1$-C$_{12}$ carbon atoms, or a monocyclic aromatic moiety, such as phenyl, or tolyl; each y is independently an integer from 0 to about 12; each l is independently an integer from 0 to about 6: and j is an integer from 1 to about 6. Some examples of reactant amines which satisfy this formula include piperazine, N-(2-aminoethyl)piperazine, N,N'-bis(2-aminoethyl)-piperazine, bis(piperazinyl)ethane, and N-(2-aminoethyl)bispiperazine. Preferably, R is hydrogen. More preferably, R is hydrogen, y is 1 or 2, j is 1 or 2, l is 0-2, and B is NR. Most preferably, each R is hydrogen, y is 0, j is 1, and each l is 0, and the compound is piperazine.

In accordance with the process of this invention, any mole ratio of reactant amine to difunctional aliphatic alcohol which enables the amination reaction to proceed to the desired alcohol-extended or amine-extended piperazine products is suitable. Typically, the difunctional aliphatic alcohol is reacted with at least about one mole equivalent of reactant amine: however, an excess of reactant amine can be advantageously employed. Preferably, the mole ratio of reactant amine to difunctional alcohol is in the range from about 0.1 to about 20. More preferably, the mole ratio of reactant amine to difunctional alcohol is in the range from about 1 to about 15; most preferably from about 2 to about 10.

Although, preferably, a solvent is not used in the amination reaction, it is within the scope of the invention for a solvent to be used, if desired. Any solvent is acceptable provided that (1) it is not reactive with the difunctional alcohol, the reactant amine, or product piperazines, and (2) it does not decompose under the conditions of the reaction. Some examples of suitable solvents include water, saturated aliphatic hydrocarbons such as pentane, hexane, heptane, octane, nonane, and decane, and aromatic hydrocarbons such as benzene, toluene, and xylene. The amount of solvent employed depends on the particular reactants and reaction conditions. Any amount of solvent is acceptable that meets the intended purpose of use. Typically, the solvent constitutes from about 5 weight percent to about 95 weight percent of the feed stream. Preferably, the solvent constitutes from about 10 weight percent to about 80 weight percent of the feed stream.

The catalyst employed in the process of this invention contains a tungsten heteropoly acid. Heteropoly acid anions are comprised of oxygen, a framework atom, and one or two atoms of a third element known as the heteroatom. In the heteropoly acid catalysts of this invention, the framework atom is tungsten. It is within the scope of this invention for one or two atoms of the tungsten cluster to be substituted with a second framework metal, such as Ti, Zr, V, Nb, Ta, Mo, Mn, Fe, Co, Ni, and Cu. Such substituted framework clusters are still predominately tungsten clusters. The heteroatom is an element from Groups IIIA, IVA, VA, VIA, the transition elements, or the rare earth lanthanide and actinide metals of the Periodic Table. Examples of suitable heteroatoms include P, Si, Ga, Al, As, and Ge, as well as B, Co, Ce, Pr, U, and Th. The heteropoly acid can be employed in its acid form or as a metal salt, either of which can also be hydrated. The degree of water associated with the tungsten heteropoly acid can vary depending upon whether the heteropoly acid has been dried, and if dried, at what temperature. Preferably, the tungsten heteropoly acid of this invention is represented by the general formula:

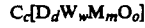

wherein C is the counter cation, typically $H^+$, $NH_4^+$, quaternary ammonium salts such as tetra(octyl)ammonium (+1), or any metallic cation such as $K^+$, $Co^{+2}$, $Cu^{+2}$, or mixtures of the above: D is the heteroatom: W is tungsten, the framework atom: M is an additional framework atom, and O is oxygen. The letters c, d, w, m, and o are each numbers which identify the number of atoms of the corresponding element per molecular formula of the cluster. Preferably, d is a positive integer from 1 to 3; w is a positive integer from about 8 to about 40; m is an integer from 0 to 2; and o is a positive integer from about 20 to about 100. The letter c represents a positive number sufficient to maintain overall charge neutrality by balancing the charge of the anion. Examples of suitable tungsten heteropoly acids, which satisfy the above-identified formula, include but are not limited to: $H_3[PW_{12}O_{40}]$, $H_4[SiW_{12}O_{40}]$, $Na_3[PW_{12}O_{40}]$, $(NH_4)_3[PW_{12}O_{40}]$, $H_2Na[PW_{12}O_{40}]$, $Co_{3/2}[PW_{12}O_{40}]$, $Al[PW_{12}O_{40}]$; as well as heteropolytungstates having the polyoxoanion cluster $[P_2W_{18}O_{62}]^{6-}$, such as $H_6[P_2W_{18}O_{62}]$; open framework structures having other than 12 or 18 framework metal ions, such as $H_7[PW_{11}O_{39}]$, $K_7[PW_{11}O_{39}]$, $K_8[SiW_{11}O_{39}]$, and $K_8GeW_{11}O_{39}]$; as well as triheteropoly acids such as $H_4[VPW_{11}O_{40}]$ and $H_5[V_2PW_{10}O_{40}]$, $K_5[MnPW_{11}O_{39}]$, $K_5[CoPW_{11}O_{39}]$, and $K_5[CuPW_{11}O_{39}]$. Preferably, the heteroatom is P or Si, and the heteropoly acid is a tungstophosphoric acid or tungstosilicic acid, respectively. More preferably, the heteropoly acid is a tungstophosphoric acid. Even more preferably, the heteropoly acid is a 12-tungstophosphoric acid species, which means that the tungsten/phosphorus mole ratio is 12/1. Most preferably, the heteropoly acid is $H_3[PW_{12}O_{40}]$.

The heteropoly acids of this invention can be purchased commercially or synthesized by procedures documented in the art. See, for example, *Comprehensive Inorganic Chemistry*, Vol. 3, A. F. Trotman-Dickenson et al., eds., Pergamon, Press, Oxford, 1973, pp. 767–768, and references therein.

The tungsten heteropoly acid can be soluble in the reaction mixture, and therefore, can act as a homogeneous catalyst. Alternatively, the tungsten heteropoly acid can be insoluble in the reaction mixture, and therefore, can act as a heterogeneous catalyst. The solubility of the tungsten heteropoly acid varies depending upon the specific alcohol and amine reactants, the specific cation associated with the heteropoly anion, and the size of the heteropoly anion. Preferably, the heteropoly acid is insoluble and acts as a heterogeneous catalyst, because then it is easier to separate from the product stream.

One preferred method of ensuring that the tungsten heteropoly acid is insoluble in the reaction mixture is by applying the heteropoly acid to a support material. Any support material is acceptable provided that it does not hinder the formation of the desired alcohol-extended or amine-extended piperazines in the process of this invention. Suitable supports include carbon and refractory oxides such as alumina, zirconia, boria, thoria, magnesia, titania, tantala, chromia, silica, kielselguhr, niobia, zeolites, as well as mixtures thereof. Preferably, the support material is titania. The support material typically has a surface area of at least about 0.1 $m^2/g$. Preferably, the support material has a surface area in the range from about 5 $m^2/g$ to about 600 $m^2/g$; and most preferably in the range from about 50 $m^2/g$ to about 200 $m^2/g$. These surface areas are measured by the Brunauer-Emmett-Teller (BET) method, which is described by R. B. Anderson in *Experimental Methods in Catalytic Research*, Academic Press, New York, 1968, pp. 48–66.

The tungsten heteropoly acid can be applied to the support material in any known fashion, such as the impregnation technique, or by precipitation in situ from the catalyst preparation reaction. Preferably, the resulting catalyst composition is calcined in air at a temperature below the decomposition point of the heteropoly cluster. Typically, the calcination is conducted at a temperature not greater than about 900° C. Preferably, the catalyst is calcined at a temperature between about 175° C. and about 500° C, more preferably, between about 200° C. and about 350° C. Typically, the catalyst composition is calcined for a time in the range from about 2 hours to about 24 hours. It will be understood that the phosphorus and tungsten are present on the calcined support in the form of tungstophosphoric groups. The exact nature of the chemical binding of the catalyst to the support is not completely understood; however, the support and calcination generally yield a catalyst having improved physical stability.

The amount of catalyst which is employed in the process of this invention is any amount which is effective in producing the desired alcohol-extended and amine-extended piperazines. The amount of catalyst varies considerably depending upon the specific reactants and reaction conditions employed. Typically, in a batch reactor the amount of catalyst is in the range from about 0.1 weight percent to about 20 weight percent based on the weight of reactant amine. Preferably, the amount of catalyst is in the range from about 1 weight percent to about 15 weight percent based on the weight of reactant amine.

Generally, the process of this invention can be carried out in any suitable reactor, including batch reactors, continuous fixed-bed reactors, slurry reactors, fluidized bed reactors, and catalytic distillation reactors. Preferably, the reactor is a continuous fixed-bed reactor.

The reactants are contacted with the catalyst at any operable temperature which promotes the amination process of this invention and yields the desired alcohol-extended and amine-extended piperazine products. Typically, the temperature is in the range from about 200° C. to about 350° C. Preferably, the temperature is in the range from about 250° C. to about 325° C. More preferably, the temperature is in the range from about 260° C. to about 315° C. Below the preferred lower temperature the conversion of difunctional aliphatic alcohol may be low. Above the preferred upper temperature the selectivity for alcohol-extended and amine-extended piperazines may decrease.

Likewise, the reactants are contacted with the catalyst at any operable pressure which promotes the amination process of this invention and yields the desired alcohol-extended and amine-extended piperazine products. Typically, the pressure is sufficient to maintain the reactants in the liquid state at the temperature of the reaction. Preferably, the pressure is in the range from about atmospheric to about 4000 psig. More preferably, the pressure is in the range from about 100 psig to about 3000 psig. Most preferably, the pressure in the range from about 400 psig to about 2000 psig. In batch reactors the pressure is autogenous, and depends on the vapor pressures of the reactants and products and the temperature of the reaction.

is given in units of grams of total reactants per milliliter of total reactor volume per hour, $g\ ml^{-1}\ hr^{-1}$. It is preferred to employ a liquid hourly space velocity of reactants in the range from about $0.1\ g\ ml^{-1}\ hr^{-1}$ to about $10.0\ g\ ml^{-1}\ hr^{-1}$; more preferably in the range from about $0.5\ g\ ml^{-1}\ hr^{-1}$ to about $4.0\ g\ ml^{-1}\ hr^{-1}$. It should be understood that the space velocity controls the residence time of the reactants in a continuous flow reactor.

When the process is conducted in a batch reactor, the reaction time determines the length of contact between the reactants and the catalyst. Any reaction time is acceptable which allows the amination reaction to proceed to the desired alcohol-extended and amine-extended piperazine products. The reaction time will depend on the quantity of reactants, the quantity of catalyst, the temperature of the reaction and desired degree of conversion. Preferably, the reaction time in a batch reactor is in the range from about 1 hour to about 20 hours.

When the difunctional aliphatic alcohol and the reactant amine are contacted in accordance with the process of this invention, the alcohol and the reactant amine react to form a mixture of alcohol-extended and/or amine-extended piperazine products, and water is eliminated as a by-product. These products can be further described as linearly-extended materials. If the difunctional alcohol contains two or more hydroxyl moieties, the reactant amine may react at each hydroxyl. Thus, as noted hereinbefore, ethylene glycol reacts with piperazine to yield predominately N-(2-hydroxyethyl)piperazine, an alcohol-extended piperazine; and monoethanolamine reacts with piperazine to yield predominately N-(2-aminoethyl)piperazine, an amine-extended piperazine. Higher amine-extended piperazine oligomers can also be produced, as in the reaction of piperazine with hydroxyethylpiperazine to yield bis(piperazinyl)ethane and tris(piperazinyl)ethane. Other amine-extended piperazines which can be produced in the process of this invention include N,N'-bis(2-aminoethyl)piperazine, and N,N'-bis(2-aminoethyl)bispiperazine. Other alcohol-extended piperazines which can be produced in the process of this invention include N,N'-bis(2-hydroxyethyl)-piperazine and N-(2-hydroxyethyl)bispiperazines. In addition to the linearly-extended products, it is possible to obtain certain undesirable cyclic by-products, including, for example, 1,4-diaza-2,2,2]-bicyclooctane.

The preferred alcohol-extended and amine-extended piperazine products can be represented by the general formula:

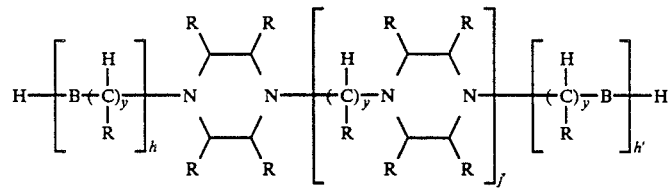

When the process is conducted in a continuous flow reactor, the flow rate of the reactants can be varied. Generally, the difunctional aliphatic alcohol and the reactant amine are premixed to form a feed stream, which is fed into the reactor at any operable flow rate which yields the desired alcohol-extended or amine-extended piperazine products. The flow rate is expressed as the liquid hourly space velocity (LHSV) and wherein each B is independently O or NR; each R is independently hydrogen, hydroxy, amino, a lower alkyl moiety of $C_1$–$C_{12}$ carbon atoms such as methyl, ethyl or propyl, a hydroxyalkyl or aminoalkyl moiety of $C_1$–$C_{12}$ carbon atoms, or a monocyclic aromatic moiety, such as phenyl, or tolyl: each y is independently an integer from 0 to about 12; h and h' are each independently integers from 0 to about 6: and j' is an integer from 0 to about 6. Some examples of products which satisfy this formula include N-(2-aminoethyl)piperazine, N-(2-hydroxyethyl)piperazine, bispiperazines and higher oligomers of piperazine. Preferably, R is hydrogen. More preferably, R is hydrogen, y is 1 or 2, j' is 1 or 2, h and h' are each independently 0-2, and B is NR. Most preferably, B is NR, R is hydrogen, y is 2, h is 1, j' and h' are each 0, and the product is N-(2-aminoethyl)piperazine.

For the purposes of this invention, "conversion" is defined as the weight percentage of difunctional aliphatic alcohol lost from the feed stream as a result of reaction. The conversion can vary widely depending upon the reactants, the form of the catalyst, and the process conditions such as temperature, pressure, and flow rate. Within the preferred temperature range, as the temperature increases the conversion typically increases. Within the preferred space velocity range, as the space velocity increases the conversion typically decreases. Typically, the conversion of the difunctional alcohol is at least about 3 weight percent. Preferably, the conversion is at least about 10 weight percent; more preferably at least about 30 weight percent; even more preferably, 45 weight percent; and most preferably, at least about 55 weight percent.

Likewise, for the purposes of this invention "selectivity" is defined as the weight percentage of converted difunctional alcohol which forms a particular alcohol-extended or amine-extended piperazine product. Typically, the selectivities also vary widely depending upon the reactants, the form of the catalyst, and the process conditions. Within the preferred temperature range, as the temperature increases the selectivity for alcohol-extended and amine-extended piperazines typically decreases. Within the preferred space velocity range, as the space velocity increases, the selectivity for alcohol-extended and amine-extended piperazines typically increases. Typically, the process of this invention achieves high selectivities to alcohol-extended and amine-extended piperazines. Preferably, the combined selectivity to alcohol-extended and amine-extended piperazines is at least about 50 weight percent, more preferably, at least about 65 weight percent, most preferably, at least about 80 weight percent. In the specific amination of monoethanolamine by piperazine, the product N-(2-aminoethyl)piperazine is produced in a selectivity of at least about 30 weight percent, more preferably, at least about 50 weight percent, most preferably, at least about 60 weight percent.

The following examples illustrate the invention, but are not intended to be limiting thereof. All percentages are given as weight percent, unless noted otherwise. In some instances the following abbreviations are used to indicate the reactants and products:

| | |
|---|---|
| MEA | monoethanolamine |
| EDA | ethylenediamine |
| AEEA | N-(2-aminoethyl)ethanolamine |
| DETA | diethylenetriamine |
| TETA | triethylenetetramine |
| PIP | piperazine |
| AEP | N-(2-aminoethyl)piperazine |
| DIAEP | N,N'-di(2-aminoethyl)piperazine |
| PEEDA | (piperazinylethyl)ethylenediamine |
| BISPIP | bispiperazine or 1,2-bis(piperazinyl)ethane |
| DABCO | 1,4-diazabicyclo-[2.2.2]-octane |

EXAMPLE 1

(a) Preparation of Catalyst

12-Tungstophosphoric acid, $H_3[PW_{12}O_{40}] \cdot 10.8\%$ $H_2O$, (2.012 g; Alfa) is dissolved in 50 ml of acetonitrile to form a solution. Titania (20.004 g; SAKI CS-200) is added to the solution, and the mixture is rotated on a rotary evaporator while the solvent is removed. The dry solid is heated under air at 200° C. overnight to yield a titania-supported tungstophosphoric acid catalyst.

(b) Amination of Monoethanolamine

The titania-supported tungstophosphoric acid catalyst (30.0 g), prepared hereinabove, is loaded into a stainless steel tubular, fixed-bed, continuous flow reactor (approximately 20 cm³ volume) fitted at both ends with glass wool plugs. A feed stream comprising monoethanolamine, piperazine, water, and optionally, ethylenediamine and diethylenetriamine is passed through the catalyst bed at a variety of reaction temperatures, pressures, and flow rates. (See Table I.) The liquid effluent from the reactor is collected and sampled by gas phase chromatography. An SE-54 capillary column (30 m×0.25 mm dia.) is employed to measure total amine products. Isomer distributions are measured on an SE-30 capillary column (30 m×0.25 mm dia.). The process conditions and results are presented in Table I.

TABLE I

| | Feed (GC area % based on organics) [1] | | | | MEA/PIP mole ratio | Temp. (°C.) | P (psig) | LHSV g ml$^{-1}$ hr$^{-1}$ | % MEA Conv. |
|---|---|---|---|---|---|---|---|---|---|
| Ex. 1 | EDA | MEA | PIP | DETA | | | | | |
| a | 0.266 | 31.576 | 67.831 | 0 | 1.0 | 285 | 1400 | 0.85 | 37.3 |
| b | 0.266 | 31.576 | 67.831 | 0 | 1.0 | 300 | 1400 | 1.05 | 50.6 |
| c | 0.266 | 31.576 | 67.831 | 0 | 1.0 | 300 | 1430 | 1.05 | 42.0 |
| d | 0 | 48.032 | 51.968 | 0 | 2.0 | 300 | 1430 | 1.05 | 47.8 |
| e | 7.241 | 30.307 | 53.764 | 7.676 | 1.3 | 315 | 1400 | 0.95 | 67.9 |
| f | 7.807 | 17.900 | 63.889 | 8.577 | 2.0 | 300 | 1400 | 1.05 | 32.1 |
| g | 7.241 | 30.307 | 53.764 | 7.676 | 1.3 | 300 | 1400 | 1.05 | 68.7 |

| | Selectivity [2] | | | | | | | | |
|---|---|---|---|---|---|---|---|---|---|
| EX. 1 | EDA | DETA | AEEA | AEP | Linear TETA | DIAEP | PEEDA | BISPIP | OTHER [3] |
| a | 0 | 0 | 8.55 | 65.06 | 0 | 5.26 | 7.15 | 2.51 | 11.46 |
| b | 0 | 0 | 6.51 | 64.44 | 0 | 7.14 | 7.94 | 2.94 | 11.01 |
| c | 0.43 | 0.27 | 7.74 | 66.27 | 0 | 7.70 | 8.09 | 2.39 | 7.11 |
| d | 1.12 | 0 | 13.40 | 52.68 | 0 | 7.20 | 7.67 | 1.52 | 16.40 |
| e | 0 | 0 | 4.57 | 49.34 | 0 | 7.24 | 8.57 | 1.31 | 28.99 |
| f | 0 | 0 | 6.41 | 66.31 | 6.74 | 2.68 | 5.99 | 0.42 | 11.45 |

TABLE I-continued

| g | 0 | 0 | 4.65 | 47.50 | 0 | 7.09 | 8.57 | 1.29 | 30.90 |

[1] Additionally, the feed contains 18–20 weight percent water.
[2] Calculated on feed-free and $H_2O$-free basis from GC area percentages corrected for individual response factors.
[3] Other products include branched TETA, linear and branched TEPA, higher piperazinyl homologs, and in (e) and (g) small amounts of ethylamine. No DABCO is found in the product streams.

The data show that the conversion of monoethanolamine increases as the reaction temperature increases. Moreover, the products which are formed are predominately alcohol-extended and amine-extended piperazines.

What is claimed is:

1. A process for preparing alcohol-extended and amine-extended piperazines comprising contacting a difunctional aliphatic alcohol with a reactant amine, the difunctional alcohol having at least one hydroxyl moiety bound to a primary carbon atom and at least one additional moiety selected from the group consisting of hydroxyl, primary amine and secondary amine functionalities, and wherein at least one of the difunctional alcohol or reactant amine contains a piperazine moiety, the contacting occurring in the presence of a catalyst under reaction conditions such that a mixture of alcohol-extended and/or amine-extended piperazines is formed, said catalyst containing a tungsten heteropoly acid.

2. The process of claim 1 wherein the difunctional alcohol is represented by the formula

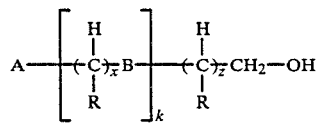

wherein A is OH or NHR; each B is independently NR or O; each R is independently hydrogen, hydroxy, amino, a lower alkyl moiety of $C_1$-$C_{12}$ carbon atoms, a hydroxyalkyl or aminoalkyl moiety of $C_1$-$C_{12}$ carbon atoms, or a phenyl or tolyl moiety; x is an integer from 2 to about 12; k is an integer from 0 to about 150; and z is an integer from 1 to about 12.

3. The process of claim 2 wherein R is hydrogen.

4. The process of claim 3 wherein x is 2 and z is 1.

5. The process of claim 4 wherein R is hydrogen, A is $NH_2$, k is 0, z is 1, and the difunctional alcohol is monoethanolamine.

6. The process of claim 1 wherein the difunctional alcohol is represented by the formula:

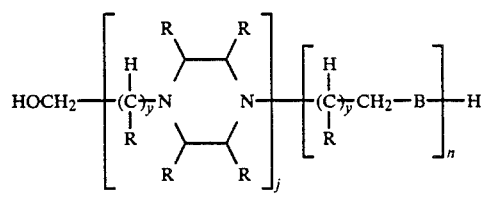

wherein each B is independently NR or O; each R is independently hydrogen, hydroxy, amino, a lower alkyl moiety of $C_1$-$C_{12}$ carbon atoms, a hydroxyalkyl or aminoalkyl moiety of $C_1$-$C_{12}$ carbon atoms, or a phenyl or tolyl moiety; each y is independently an integer from 0 to about 12; j is an integer from 1 to about 6; and n is an integer from 0 to about 6.

7. The process of claim 6 wherein R is H, y is 1, j is 1 and n is 0, and the difunctional alcohol is N-(2-hydroxyethyl)piperazine.

8. The process of claim 1 wherein the reactant amine is represented by the formula:

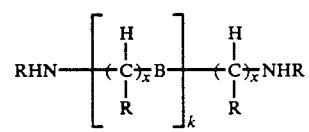

wherein each B is independently NR or O; each R is independently hydrogen, hydroxy, amino, a lower alkyl moiety of $C_1$-$C_{12}$ carbon atoms, a hydroxyalkyl or aminoalkyl moiety of $C_1$-$C_{12}$ carbon atoms, or a phenyl or tolyl moiety; each x is independently an integer from 2 to about 12; and k is an integer from 0 to about 150.

9. The process of claim 8 wherein the reactant amine is an ethylenepolyamine.

10. The process of claim 1 wherein the reactant amine is represented by the formula:

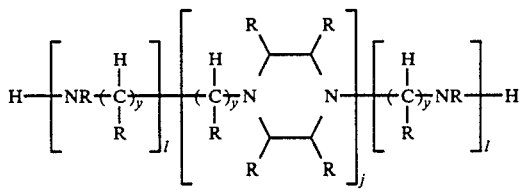

wherein each R is independently hydrogen, hydroxy, amino, a lower alkyl moiety of $C_1$-$C_{12}$ carbon atoms, a hydroxyalkyl or aminoalkyl moiety of $C_1$-$C_{12}$ carbon atoms, or a phenyl or tolyl moiety; each y is independently an integer from 0 to about 12; each l is independently an integer from 0 to about 6; and j is an integer from 1 to about 6.

11. The process of claim 10 wherein R is hydrogen, y is 0, j is 1, each l is 0, and the compound is piperazine.

12. The process of claim 1 wherein the mole ratio of reactant amine to difunctional aliphatic alcohol is at least about 1.

13. The process of claim 1 wherein the catalyst is represented by the formula $C_c[D_dW_wM_mO_o]$ wherein C is the counter cation, D is the heteroatom selected from the group consisting of the elements of Groups IIIA, IVA, VA, VIA, the transition elements and the rare earth lanthanide and actinide metals of the Periodic Table, W is tungsten, M is an additional framework atom selected from the group consisting of Ti, Zr, V, Nb, Ta, Mo, Mn, Fe, Co, Ni, and Cu, and O is oxygen, and wherein d is an integer from 1 to 3, w is an integer from about 8 to about 40, m is an integer from 0 to 2, and o is an integer from about 20 to about 100, and c is a number sufficient to maintain overall charge neutrality by balancing the charge of the anion.

14. The process of claim 13 wherein the heteroatom is P or Si.

15. The process of claim 14 wherein the heteropoly acid is a 12-tungstophosphoric acid.

16. The process of claim 15 wherein the heteropoly acid is $H_3[PW_{12}O_{40}]$.

17. The process of claim 1 wherein the amount of catalyst is in the range from about 0.1 weight percent to about 20 weight percent based on the weight of reactant amine.

18. The process of claim 1 wherein the temperature is in the range from about 200° C. to about 350° C.

19. The process of claim 1 wherein the pressure is in the range from about atmospheric to about 4000 psig.

20. The process of claim 1 wherein the liquid hourly space velocity is in the range from about $0.1 \text{ g ml}^{-1} \text{ hr}^{-1}$ to about $10.0 \text{ g ml}^{-1} \text{ hr}^{-1}$.

21. The process of claim 1 wherein the alcohol-extended and amine-extended piperazines are represented by the formula:

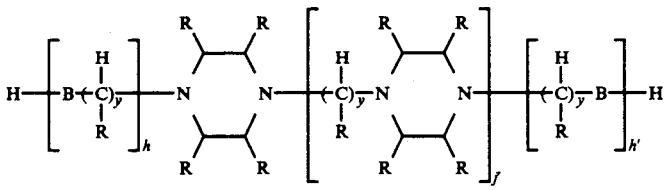

wherein each B is independently O or NR; each R is independently hydrogen, hydroxy, amino, a lower alkyl moiety of $C_1$–$C_{12}$ carbon atoms, a hydroxyalkyl or aminoalkyl moiety of $C_1$–$C_{12}$ carbon atoms, or a phenyl or tolyl moiety; each y is independently an integer from 0 to about 12; h and h' are independently integers from 0 to about 6; and j' is an integer from 0 to about 6.

22. The process of claim 21 wherein B is NR, R is hydrogen, y is 2, h is 1, j' and h' are 0, and the product is N-(2-aminoethyl)piperazine.

23. A process for preparing N-(2-aminoethyl)piperazine comprising contacting monoethanolamine with piperazine in the presence of a catalyst containing titania-supported 12-tungstophosphoric acid under conditions sufficient to prepare N-(2-aminoethyl)piperazine in a selectivity of at least about 30 weight percent.

24. The process of claim 23 wherein the N-(2-aminoethyl)piperazine is produced in a selectivity of at least about 50 weight percent.

25. The process of claim 24 wherein the N-(2-aminoethyl)piperazine is produced in a selectivity of at least about 60 weight percent.

26. A process for preparing alcohol-extended and amine-extended piperazines comprising contacting a difunctional aliphatic alcohol with a reactant amine, wherein the difunctional aliphatic alcohol is selected from the group consisting of polyols, alkanolamines, polyether amino alcohols, and hydroxyalkyl-substituted piperazines, and wherein at least one of the difunctional alcohol or the reactant amine contains a piperazine moiety, the contacting occurring in the presence of a catalytic amount of a tungsten heteropoly acid wherein the heteroatom is P or Si and under reaction conditions such that a mixture of alcohol-extended and/or amine-extended piperazines is formed.

* * * * *